United States Patent [19]
McDonald

[11] Patent Number: 6,096,078
[45] Date of Patent: Aug. 1, 2000

[54] ACCOMMODATIVE LENS IMPLANTATION

[75] Inventor: Henry H. McDonald, Rancho Mirage, Calif.

[73] Assignee: Surgical Concepts, Inc., Newport Beach, Calif.

[21] Appl. No.: 09/198,254

[22] Filed: Nov. 24, 1998

Related U.S. Application Data

[63] Continuation of application No. 08/954,656, Oct. 20, 1997, Pat. No. 5,843,188.

[51] Int. Cl.$^7$ ........................................... A61F 2/16
[52] U.S. Cl. ........................................... 623/6.22; 623/6.37
[58] Field of Search ........................... 623/6, 6.22, 6.11

[56] References Cited

U.S. PATENT DOCUMENTS

| | | |
|---|---|---|
| 4,198,714 | 4/1980 | Jensen . |
| 4,304,012 | 12/1981 | Richard ........................... 623/6 |
| 4,414,694 | 11/1983 | Choyce . |
| 4,441,217 | 4/1984 | Cozean, Jr. . |
| 4,573,998 | 3/1986 | Mazzocco . |
| 4,585,456 | 4/1986 | Blackmore ....................... 623/6 |
| 4,605,409 | 8/1986 | Kelman . |
| 4,731,078 | 3/1988 | Stoy et al. . |
| 4,769,035 | 9/1988 | Kelman . |
| 4,786,445 | 11/1988 | Portnoy et al. . |
| 4,790,846 | 12/1988 | Christ et al. . |
| 4,813,957 | 3/1989 | McDonald . |
| 4,816,031 | 3/1989 | Pfoff ................................. 623/6 |
| 4,834,751 | 5/1989 | Knight et al. . |
| 4,840,627 | 6/1989 | Blumenthal . |
| 4,842,602 | 6/1989 | Nguyen . |
| 4,880,426 | 11/1989 | Ting et al. . |
| 4,888,013 | 12/1989 | Ting et al. . |
| 4,888,014 | 12/1989 | Nguyen . |
| 4,894,062 | 1/1990 | Knight et al. . |
| 4,932,970 | 6/1990 | Portney . |
| 4,938,767 | 7/1990 | Ting et al. . |
| 4,957,505 | 9/1990 | McDonald . |
| 4,959,070 | 9/1990 | McDonald . |
| 4,978,354 | 12/1990 | Van Gent . |
| 5,030,231 | 7/1991 | Portney . |
| 5,044,743 | 9/1991 | Ting . |
| 5,098,444 | 3/1992 | Feaster ........................... 623/6 |
| 5,108,429 | 4/1992 | Wiley ............................. 623/6 |
| 5,171,266 | 12/1992 | Wiley et al. .................... 623/6 |
| 5,203,788 | 4/1993 | Wiley ............................. 623/6 |
| 5,203,789 | 4/1993 | McDonald . |
| 5,203,790 | 4/1993 | McDonald . |
| 5,217,464 | 6/1993 | McDonald . |
| 5,258,025 | 11/1993 | Fedorov ......................... 623/6 |
| 5,395,378 | 3/1995 | McDonald . |
| 5,405,385 | 4/1995 | Heimke et al. ................. 623/6 |
| 5,476,514 | 12/1995 | Cumming . |
| 5,480,428 | 1/1996 | Fedorov et al. ................ 623/6 |
| 5,578,081 | 11/1996 | McDonald . |
| 5,800,530 | 9/1998 | Rizzo ............................. 623/6.22 |

FOREIGN PATENT DOCUMENTS

| | | |
|---|---|---|
| 4131229 | 1/1993 | Germany . |

OTHER PUBLICATIONS

"Polyseudophakia" by Harry B. Grabow published Jul., 1977, pp. 1–6.

"Achieving Emmetropia in Extremely Short Eyes With Two Piggyback Posterior Chamber Intraocular Lenses", by Jack T. Holladay et al, published in "Ophthalmology", vol. 103, No. 7 Jul., 1996, pp. 1118–1123.

"Two Iols Better Than One For High Hyperopes" by Leslie Sabbagh, published Nov. 1, 1994, Ophthalmology Times.

"Implanting Two Posterior Chamber Intraocular Lenses in Microthalmos" by Dr. J. L. Gayton, published in "Ocular Surgery News", 1994, pp. 64 & 65.

*Primary Examiner*—David H. Willse
*Attorney, Agent, or Firm*—William W. Haefliger

[57] ABSTRACT

A method of providing an artificial lens inserted into the eye between the iris and the natural lens zone, there being eye ciliary muscles located peripherally of the zone, that includes providing the artificial lens to be compliant and to have anterior and posterior surfaces, and haptics extending away from the periphery of the artificial lens; and inserting the artificial lens to extend into position between the iris and the zone, and to cause the haptics to extend into adjacency to the ciliary muscles, and; allowing the haptics to adhere to the ciliary muscles; whereby subsequent movement of the ciliary muscles causes movement of the haptics transmitted to effect bodily movement of the lens in posterior and anterior directions to change the angularity of refraction of light passing through the lens toward the eye retina.

7 Claims, 3 Drawing Sheets

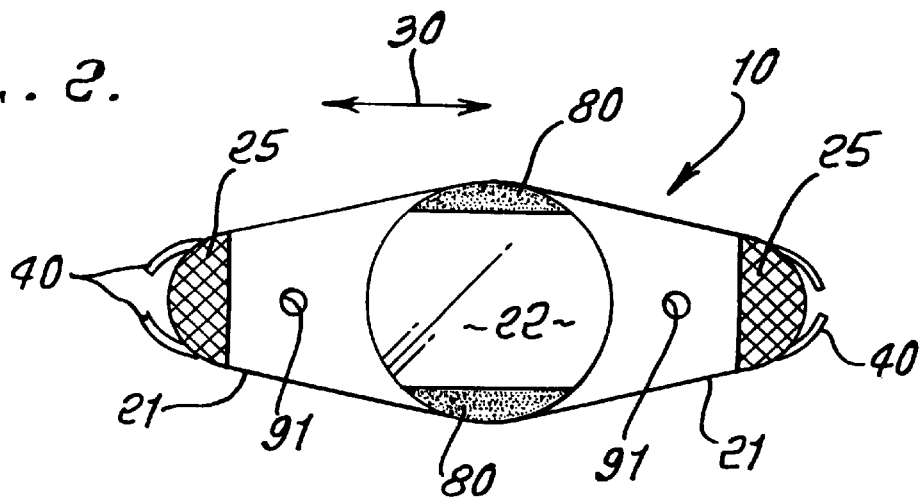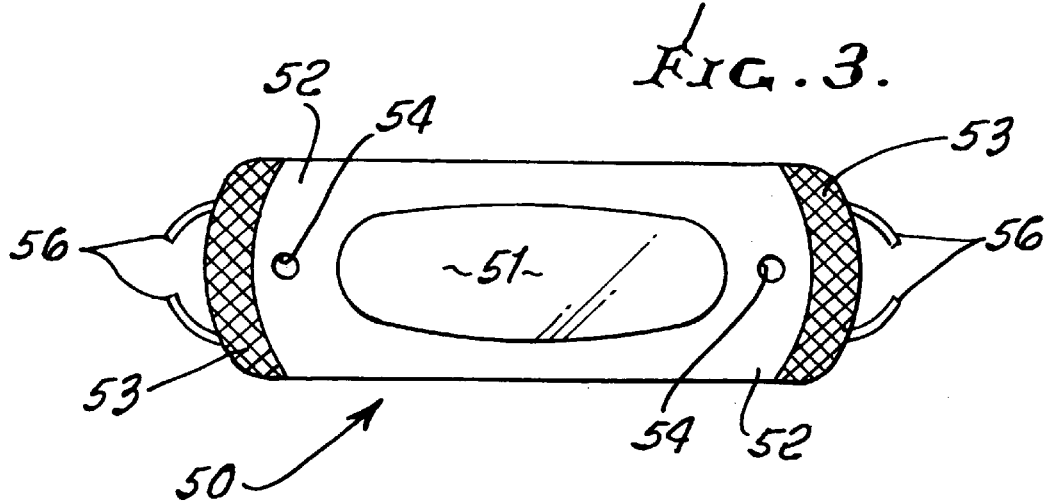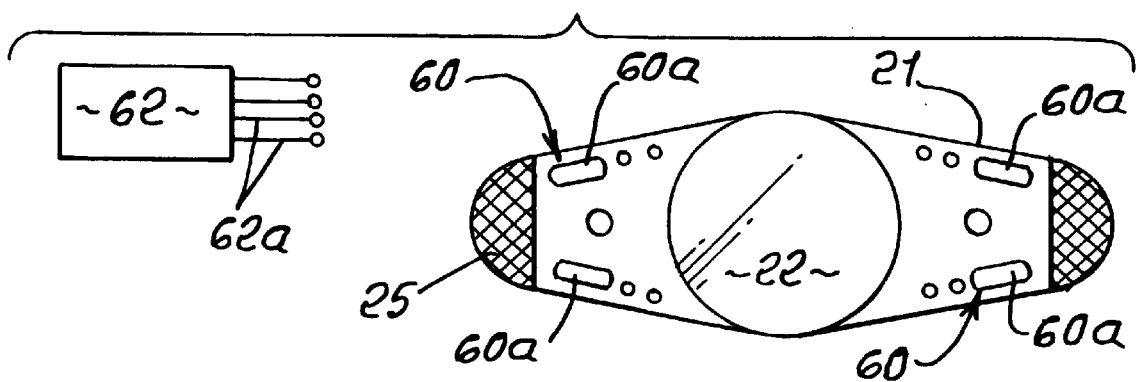

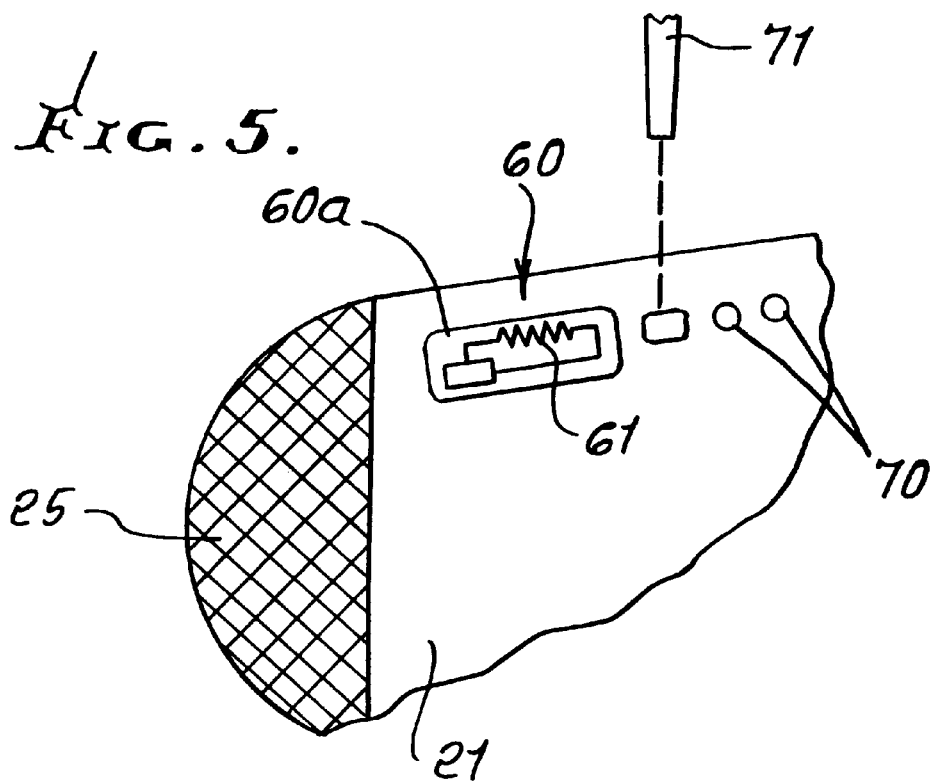
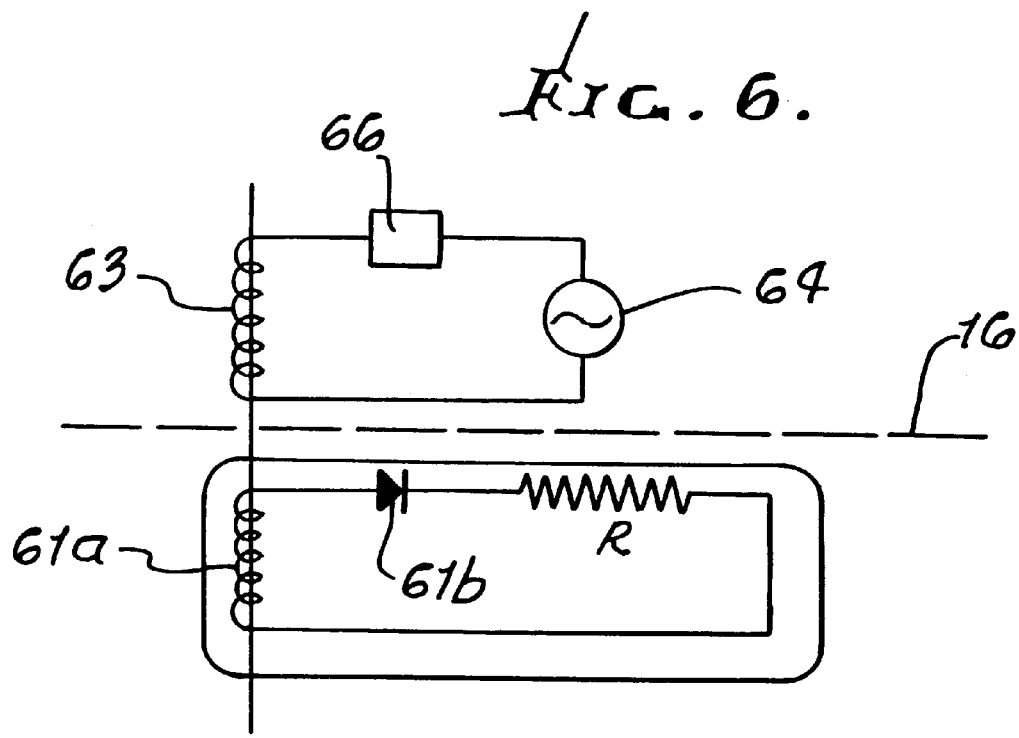

ACCOMMODATIVE LENS IMPLANTATION

This application is a continuation of U.S. application Ser. No. 08/954,656, filed on Oct. 20, 1997, now U.S. Pat. No. 5,843,188.

BACKGROUND OF THE INVENTION

This invention relates generally to implantation of artificial lenses in the eyes of humans, and/or animals, and more particularly concerns implantation of such lenses in the posterior chambers of the eyes, i.e., between the iris and the natural lens zone. That zone may contain a natural lens, or an artificial lens, such as a pseudophakic lens.

It is known to insert artificial lenses into posterior chambers of eyes; however, prior implantations have suffered from difficulties. These have included presumed need for attaching or anchoring the artificial lens directly onto a surface of the pseudophakic lens, as by bonding, or by clipping mechanism. These expedients can or do interfere with vision and lens movement. There is need for method and apparatus that avoids such problems and difficulties. There is also need for implantation of lenses capable of movement toward or away from the natural lens zone as will be referred to herein.

SUMMARY OF THE INVENTION

It is a major object of the invention to provide implantation of a vision correcting artificial lens into the eye posterior chamber, and in such manner as to avoid problems and difficulties, as referred to. Basically, the method of the invention includes the steps:

a) providing the artificial lens to be compliant and to have anterior and posterior surfaces, and haptics extending away from the periphery of the artificial lens, b) and inserting the artificial lens to extend into position between the iris and the natural lens zone, and to cause the haptics to extend into adjacency to the ciliary muscles, and c) allowing the haptics to adhere or attach to the ciliary muscles, to move in response to ciliary muscle movement.

Such adherence may be achieved by adherence of haptic outer surfaces to zonular ligaments and/or onto fascia of the ciliary muscles, thereby positioning the artificial lens close to the surface of the pseudophakic lens; and so that clarity of vision is not interrupted by bonding zones, or clip devices to hold the lens in place, such bonding and clips not being needed.

It is another object to position the inserted lens in the manner referred to whereby subsequent movement of the ciliary muscles causes movement of the haptics, transmitted to effect bodily movement of the lens in posterior and anterior directions, to change the angularity of refraction of light passing through the lens toward the eye retina, i.e., adapting to near and far vision.

The invention achieves one or more of the following advantages:

a) enables haptics to be placed in the uncluttered territory of the anterior aspect of the posterior ciliary sulcus;

b) allows placement of an elongated, asymmetric lens implant across the eye chamber to position the haptics for fixation onto zonular ligaments and/or into the fascia of the ciliary muscle;

c) affords conforming of a lens implant posterior surface over the pseudophakic lens, with haptics that extend laterally to anchor onto the available plateau at the ciliary sulcus, the fascia of the ciliary muscle, and/or onto the inert zonular ligaments;

d) allows haptics to achieve a distinctive leverage over and control of the lens optic segment, even with a mildly weak ciliary muscle;

e) affords the opportunity of using the advantages of the clear, temporal corneal wound for lens insertion without previous scarring;

f) provides an axis of astigmatism, and prisms, or other means, for correcting diplopia with particular haptic edge designs;

g) provides separability of the implanted lens from the pseudophakic lens, to:
  1) enable recoverability of the lens with ease, if necessary;
  2) maintain eye aqueous humor lateral flow behind the implanted lens without need for a central apical puncture or hole, which can detract from the clear vision;
  3) separated independent functioning of the implanted lens, without impairment from the encased pseudophakic lens entrapped in the lens capsule;
  4) allows laser titrateable (effected) alterations in the supportive elastimed band of an elongated, rectangular (i.e., asymmetric) lens implant, such as adjustments to accommodate to:
    a) the need for sufficient separability of the lens implant;
    b) the need for lens re-positioning, post-operatively;
    c) the stiffness of the haptics in control of the optic segment, as desired;

h) provides for more natural passage of aqueous humor between the pseudophakic and implanted lenses; accommodation of the lens implant is enhanced by conformance to the natural lens configuration that exists, particularly in the realm of the autonomic nerve system, and pertaining to accommodative reflex;

i) components for the errancy of the pseudophakic lens needs, such as light-blocking function of the lens implant for glare and U-V exposure, in addition to refractive corrections for astigmatism, diplopia, anisometropia, and for severe and mild degrees of myopia and hyperopia, and loss of accommodation;

j) use of the implant lens can become preferred, in view of the case of a five minute, very accurate, operative implant procedure, which is readily reversible, if ever necessary, and having the added advantage of quick relief of pain and restoration of clear vision in hours, and full rehabilitation by the next morning;

k) the range of useful indications for this lens implant are startling and may require or enable a combination of seven to eight different lens implants in one lens implant procedure, to achieve a desired vision result;

l) the ciliary muscle having a leveraged effect on the optic segment through the angle of approach of the lateral and posterior design and stiffening of the haptic, as well as adhesive, restraint on the optic segment to prevent excessive forward advancement of the optic segment by the addition of adhesive haptic edges, which also thickens the A-P diameter of the lens to assist in accommodation.

A further object includes detecting and modifying a physical characteristic of the lens inserted into the eye. Miniature electronic circuitry implants on the lens unit, as via a wafer or wafers, may be employed in such determination, and/or modification.

DRAWING DESCRIPTION

FIGS. 2–4 show artificial lens;

FIG. 5 is an enlarged fragmentary view of a lens unit haptic with electronic circuitry thereon; and FIG. 6 is a schematic circuit diagram.

DETAILED DESCRIPTION

Figure 1:
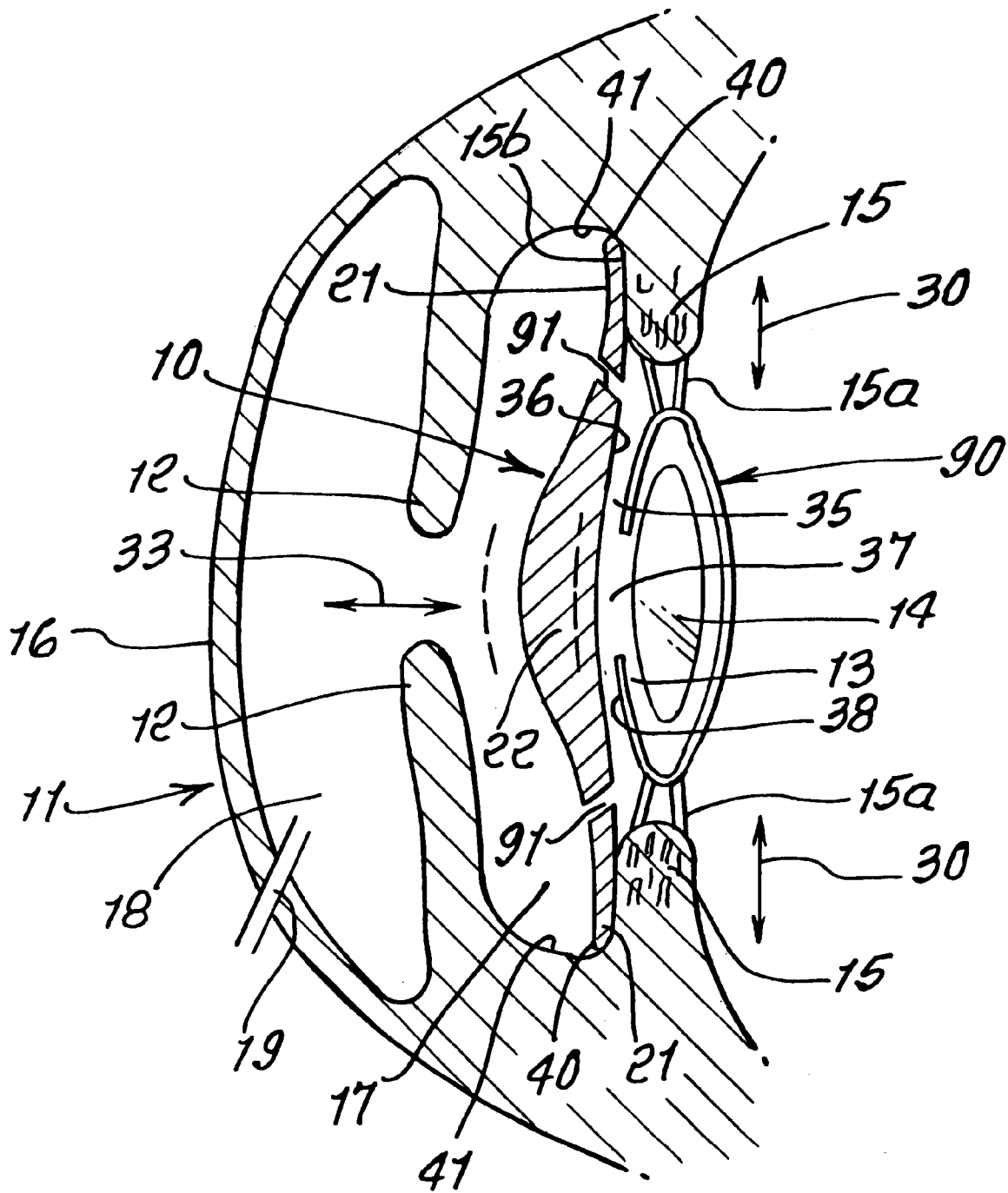
FIG. 1 is a cross section through the eye showing lens unit implantation.

In FIG. 1, the artificial lens unit 10 has been implanted into the eye 11 between the iris 12 and the natural lens zone 13. That zone is shown as including a capsule 90 from which the natural lens has been removed, and a pseudophakic (initially inserted) artificial lens 14 inserted in the capsule. The purpose for inserting lens unit 10 is to improve vision, as by correcting for vision defect associated with artificial lens 14 alone. Eye ciliary muscles are indicated at 15; and they surround the capsule to which they are peripherally attached, as at 15a. The pupil appears at 16. Posterior and anterior eye zones appear at 17 and 18.

A wound 19 in the pupil affords entry of the folded artificial lens unit 10 into the zone 18, from which it is maneuvered into zone 17, to the position shown. Haptics 21 do not engage the iris.

Lens unit 10, which may consist of silicone or equivalent material, has haptics 21, which extend oppositely away from the bead-like lens 22 in front of lens 14. See FIG. 1, for example. The haptics are or become attached or adhered to the forward-facing sides of the ciliary muscles, as at 15b, which provide a platform for haptic attachment. In this regard, the tabular haptics may have roughened surface extents, to face and engage the ciliary muscles, promoting adherence, as via eye tissue growth. One preferred example of such roughened surface extent is the mesh indicated at 25 in FIG. 2.

The haptics have sufficient stiffness to move laterally (see arrows 30) with the ciliary muscles, whose movement controls lateral contraction of the capsule, such lateral movement of the haptics being transmitted to the bulging lens bead 22, to effect its axial longitudinal deflection in the direction of arrows 33. Such deflection is sufficient to cause the lens 22 to refract light rays from an observed object to again focus at a point near the wearer's retina. Also, such lens deflection to obtain proper focusing is made possible by the initial angularity of the haptics, by the stiffness along their lateral extents, and by haptics effective hinging connection to the lens 22, along the bendable, lateral extents of the haptics, between 22 and 21. See FIG. 2.

Note the slight gap 35 between the rear surface 36 of the lens unit 10 and the front window 37 in the capsule, or the capsule surface 38 about the window. The gap contains eye fluid to wet the lenses; and a port or ports 91 may be provided in the haptics to allow eye fluid flow in and out of the gap 35, as before, during, or after lens 22 bodily movement, as described. The haptics may have yieldably flexible outer tips 40 to engage the inner wall 41 of zone 17, to aid in centering the lens unit 10, relative to the lens 14, and to aid in stably positioning the haptic roughened surface portions 25 adjacent the ciliary muscles, during adherence as by tissue growth.

FIG. 3 shows an elongated lens unit 50 having an elongated, asymmetric, light-transmitting, medial lens portion 51, haptic 52 with roughened or mesh-like regions 53, for adherence to ciliary muscles, and eye fluid passing through ports 54. Haptics positioning tips appear at 56, and may be used, as at tips 40.

FIGS. 4–6 show a unique means to operatively associate electronic or electrical circuitry with the implantable lens unit. In FIG. 4, the lens unit may have a configuration the same as in FIG. 2, for example. See the same identifying numerals applied. Also provided is electrical circuitry, indicated generally at 60, as in or on a wafer 60a attached as by bonding to the lens unit, as at haptics 21. Note the local and symmetrical locations of four such wafers 60a.

An external, master control unit 62 may have electrical or magnetic communication with the circuitry on the four wafers. See four paths or connectors 62a. Microelectronic circuitry may be provided on the wafers to process data or signals. FIG. 5 shows a circuit element 61, such as a resistor. FIG. 6 shows a current source in series with the element 61, the source for example including a coil 61a and a diode 61b. A magnetic field passing through the coil generates current, rectified at 61b and passing through the resistor. An external coil 63 and AC generator 64 generates the magnetic field. See also circuitry 66. The circuitry can be embedded in the wafer and located in or on the haptic.

One example of use is to detect strain, due to deflection in the haptic. The resistor 61 effectively bonded to the haptic, as via the wafer, is stretched as the haptic deflects, changing its resistance. This changes the response to the circuitry, reflected back through coils 61a and 63 and detected at 66, whereby the amount of deflection of the haptic can be determined externally. The use of four such detectors, as at 60a in FIG. 4, and on both haptics, enables accurate determination of inserted lens responsive movement, as the eye ciliary muscles expand and contract.

Such lens movement can then be modified, i.e., "tuned" to conform to a predetermined standard, externally. See for example the lens haptic zones 70 near each wafer, and which can be deformed as by a laser beam 71, to modify local thickness or shape of the haptic, thereby slightly changing its characteristic movement. Zones 70 may, for example, consist of thermo-plastic material, subject to shape change, with temperature increase above a temperature threshold. In this way, accuracy of vision, provided by the lens insert, can be optimized. Other types of circuits 60, and uses thereof, are of course possible and are within the scope of this invention, directed to provision of microcircuitry on an implanted lens unit.

The invention enables testing for the optimum lens insert, as for example by the steps:

a) inserting a first artificial lens into the posterior zone of the eye and temporarily positioned for eye vision correction use, in conjunction with an existing lens at the eye capsule zone, b) thereafter removing the first artificial lens from the eye, and c) inserting a second and different artificial lens into the posterior zone of the eye, and positioned for temporary eye vision corrective use, in conjunction with the existing lens, d) determining that the inserted second lens is more corrective of vision than the first lens, e) and effecting attachment of the second lens to eye structure to maintain the second lens in permanent position for use.

Other existing lens can be a pseudophakic lens, or a lens, such as a natural lens of the eye.

Light-blocking darkened or opaque zones may be provided on or at or proximate the lens periphery, as for example are indicated at 80 in FIG. 2.

Sensors embedded in the elastomide (synthetic resin) of the lens unit, as for example in haptic structure, will detect activity, such as movement of the ciliary muscle, to which the haptic becomes attached, as described. For example, ciliary muscle contraction, as detected at the multiple points (four as described) of circuit sensor location, is detected, as the lens optic is advanced forwardly, by accommodation, and the reverse occurs when the optic retracts as the ciliary muscle relaxes.

Such sensors can be used to detect rotation of the toric lens. Also, maintenance of immobility of the lens unit and ciliary muscle, as desired during healing, i.e., adhesion attachment of the haptics to the ciliary muscle, can be monitored using such sensors. Local control of lens darkening, using such circuitry with current flow between selected points on the lens unit to effect such selected zone darkening is also contemplated.

I claim:

1. An artificial lens assembly insertible into the eye, that includes, in combination:
   a) a lens unit having a lens zone to transmit light, and haptic means to position the unit in the eye, and
   b) electronic circuitry carried by said haptic means,
   c) said circuitry including a strain sensor responsive to haptic means movement.

2. The combination of claim 1 wherein said circuitry includes multiple sensors to detect haptic means movement.

3. The combination of claim 2 wherein said sensors are spaced apart to sense lens unit deflection.

4. The combination of claim 1 including means spaced from said lens unit and from said sensor to transmit a signal to and/or from said circuitry.

5. The combination of claim 1 wherein said circuitry includes means to determine a physical characteristic of the lens unit when inserted in the eye.

6. The combination of claim 5 wherein said circuitry includes means for changing a physical characteristic of the lens unit when inserted into the eye, by electromagnetic transmission of energy into the eye from the exterior thereof and from the exterior of a head in which the eye is located.

7. In apparatus for detecting or controlling the physical insertion of a synthetic lens unit within the eye, the combination that includes:
   a) an electronic circuit component or components configured to be implanted in the eye, in association with a haptic projecting from a synthetic lens unit in the eye, and wherein the circuit component or components is or are everywhere spaced from the lens unit,
   b) said circuit component or components including means to effect one of the following:
      i) detect or monitor ciliary muscle movement,
      ii) detect or monitor movement of said synthetic lens unit,
      iii) detect or monitor electronic current flow through circuitry associated with said haptic,
      iv) detect or monitor changed coloration of said synthetic lens unit or a portion thereof,
      v) effect current flow through circuitry associated with said haptic.

* * * * *